(12) United States Patent
Alonso et al.

(10) Patent No.: US 11,833,161 B2
(45) Date of Patent: *Dec. 5, 2023

(54) COMPOSITIONS AND METHODS FOR TREATMENT OF SKIN INFECTIONS

(71) Applicant: Pedicis Research LLC, Portsmouth, NH (US)

(72) Inventors: Robert Alonso, North Hampton, NH (US); Lawrence Stoll, Clifton Park, NY (US)

(73) Assignee: Pedicis Research LLC, Portsmouth, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/967,470

(22) Filed: Oct. 17, 2022

(65) Prior Publication Data

US 2023/0113715 A1 Apr. 13, 2023

Related U.S. Application Data

(60) Continuation of application No. 17/666,181, filed on Feb. 7, 2022, now Pat. No. 11,504,384, which is a
(Continued)

(51) Int. Cl.
*A61K 31/60* (2006.01)
*A61K 31/045* (2006.01)
(Continued)

(52) U.S. Cl.
CPC ............... *A61K 31/60* (2013.01); *A61K 8/20* (2013.01); *A61K 8/368* (2013.01); *A61K 8/37* (2013.01);
(Continued)

(58) Field of Classification Search
None
See application file for complete search history.

(56) References Cited

U.S. PATENT DOCUMENTS

| 3,899,578 A | 8/1975 | Bird et al. | |
| 5,385,938 A * | 1/1995 | Yu | A61K 8/64 |
| | | | 514/847 |

(Continued)

FOREIGN PATENT DOCUMENTS

| DE | 1617798 A1 * | 6/1971 | ........... A61K 9/0014 |
| EP | 1685876 A1 | 8/2006 | |

(Continued)

OTHER PUBLICATIONS

ClinicalTrials.Gov, "17% salicylate versus 17% Salicylate-ethyl pyruvate for plantar foot warts", NIH, US National Library Medicine, 2012, pp. 1-7. (Year: 2012).*

(Continued)

*Primary Examiner* — Kyung S Chang
(74) *Attorney, Agent, or Firm* — Wilson Sonsini Goodrich & Rosati

(57) ABSTRACT

A pharmaceutical composition for treating skin infections is described herein. A method using a pharmaceutical composition for treating skin infections is described herein. A pharmaceutical composition for treating skin infections may comprise, in 100 parts of the composition, 1-99 parts of a pharmaceutically acceptable excipient; 99-1 parts of a keratolytic; 99-1 parts ethyl pyruvate; and 99-1 parts povidone iodine. A method for treating skin infections may comprise topical application of a composition to an infected skin cell for a treatment period.

15 Claims, 3 Drawing Sheets

Related U.S. Application Data continuation of application No. 16/128,219, filed on Sep. 11, 2018, now abandoned, which is a division of application No. 15/679,113, filed on Aug. 16, 2017, now abandoned, which is a continuation of application No. PCT/US2016/018441, filed on Feb. 18, 2016.

(60) Provisional application No. 62/119,076, filed on Feb. 20, 2015.

(51) Int. Cl.

| | | |
|---|---|---|
| *A61K 31/19* | (2006.01) | |
| *A61K 31/197* | (2006.01) | |
| *A61K 31/22* | (2006.01) | |
| *A61K 31/375* | (2006.01) | |
| *A61K 31/79* | (2006.01) | |
| *A61K 47/10* | (2017.01) | |
| *A61K 47/18* | (2017.01) | |
| *A61P 17/12* | (2006.01) | |
| *A61K 8/368* | (2006.01) | |
| *A61K 8/37* | (2006.01) | |
| *A61Q 19/00* | (2006.01) | |
| *A61K 8/81* | (2006.01) | |
| *A61K 8/20* | (2006.01) | |
| *A61K 47/38* | (2006.01) | |
| *A61P 31/20* | (2006.01) | |
| *A61K 9/00* | (2006.01) | |
| *A61K 9/06* | (2006.01) | |

(52) U.S. Cl.
CPC .......... *A61K 8/8176* (2013.01); *A61K 9/0014* (2013.01); *A61K 9/06* (2013.01); *A61K 31/045* (2013.01); *A61K 31/19* (2013.01); *A61K 31/197* (2013.01); *A61K 31/22* (2013.01); *A61K 31/375* (2013.01); *A61K 31/79* (2013.01); *A61K 47/10* (2013.01); *A61K 47/18* (2013.01); *A61K 47/38* (2013.01); *A61P 17/12* (2018.01); *A61P 31/20* (2018.01); *A61Q 19/005* (2013.01)

(56) References Cited

U.S. PATENT DOCUMENTS

| 6,051,609 | A * | 4/2000 | Yu ......................... A61K 8/498 514/847 |
| 11,504,384 | B1 | 11/2022 | Alonso et al. |
| 2004/0033963 | A1 | 2/2004 | Yu et al. |
| 2005/0036953 | A1 | 2/2005 | Arkin et al. |
| 2005/0127552 | A1 | 6/2005 | Modha et al. |
| 2007/0207222 | A1 | 9/2007 | Yu et al. |
| 2008/0312196 | A1 * | 12/2008 | Cohen ................. A61K 9/7007 514/159 |
| 2010/0048724 | A1 | 2/2010 | Birnbaum et al. |
| 2010/0173965 | A1 | 7/2010 | Masuda et al. |
| 2011/0082118 | A1 | 4/2011 | Patel et al. |
| 2011/0086109 | A1 | 4/2011 | Dever et al. |
| 2011/0087158 | A1 | 4/2011 | Cole et al. |
| 2011/0160166 | A1 | 6/2011 | Hohenstein |
| 2013/0203847 | A1 | 8/2013 | Chappell et al. |
| 2018/0092931 | A1 | 4/2018 | Alonso et al. |
| 2019/0142848 | A1 | 5/2019 | Alonso et al. |

FOREIGN PATENT DOCUMENTS

| WO | WO-2011028110 A1 | 3/2011 | |
| WO | WO-2012154740 A1 | 11/2012 | |
| WO | WO-2013122637 A1 * | 8/2013 | ............ A61K 31/79 |
| WO | WO-2016134130 A1 | 8/2016 | |

OTHER PUBLICATIONS

EPO English Translation of DE1617798A1 (Year: 1971).*
EP16753048.4 European Search Report dated Jul. 20, 2018.
Google Books. IARC Working Group on the Evaluation of Carcinogenic Risks to Human. World Health Organization. (2007): 161.
Halasz, C. L. Treatment of warts with topical pyruvic acid: with and without added 5-fluorouracil. Clinical Trial, Cutis. 62(6): 283-5 (1998).
Johnson et al., Cutaneous Warts: An Evidence-Based Approach to Therapy, American Family Physician, vol. 72, No. 4 (2005), pp. 647-652.
PCT/US2016/018441 International Search Report and Written Opinion dated Jul. 18, 2016.
U.S. Appl. No. 15/679,113 Office Action dated Dec. 4, 2020.
U.S. Appl. No. 15/679,113 Office Action dated May 3, 2021.
U.S. Appl. No. 16/128,219 Office Action dated Dec. 18, 2020.
U.S. Appl. No. 16/128,219 Office Action dated Nov. 5, 2021.
U.S. Appl. No. 17/666,181 Notice of Allowance dated Aug. 25, 2022.
U.S. Appl. No. 17/666,181 Office Action dated May 3, 2022.
U.S. Appl. No. 15/679,113 Office Action dated Jul. 27, 2018.
U.S. Appl. No. 15/679,113 Office Action dated Apr. 8, 2020.
U.S. Appl. No. 15/679,113 Office Action dated Mar. 15, 2019.
U.S. Appl. No. 16/128,219 Office Action dated Apr. 8, 2020.
U.S. Appl. No. 16/128,219 Office Action dated Sep. 16, 2019.

* cited by examiner

100 topically applying to an infection of the skin for treatment period prescribed by a physician, at ambient temperature, without using cryotherapy, a composition for treating skin infections, comprising: in 100 parts of the composition, 1-99 parts of a pharmaceutically acceptable excipient; 99-1 parts of a keratolytic; 99-1 parts ethyl pyruvate; and 99-1 parts povidone iodine, resulting in a higher cure rate than would be achieved if the infection were treated by topically applying a control composition having only the keratolytic and balance being the pharmaceutically acceptable excipient.

105

*FIG. 1*

COMPOSITIONS AND METHODS FOR TREATMENT OF SKIN INFECTIONS

CROSS-REFERENCE

This application is a continuation of U.S. patent application Ser. No. 17/666,181, filed on Feb. 7, 2022, which is a continuation of U.S. patent application Ser. No. 16/128,219, filed on Sep. 11, 1018, which is a divisional of U.S. patent application Ser. No. 15/679,113, filed on Aug. 16, 2017, which is a continuation of International Application No. PCT/US2016/018441, filed on Feb. 18, 2016, which claims the benefit of U.S. Provisional Application No. 62/119,076, filed on Feb. 20, 2015, each of which is incorporated by reference herein in its entirety.

SUMMARY OF THE INVENTION

One embodiment of the current disclosure is a pharmaceutical composition comprising: a unit dose of at least about 15 weight % of a keratolytic agent, wherein the weight % of the keratolytic agent is based on a total weight % of the composition, a molecule comprising an oxo group and an acidic group, ester thereof, salt thereof, or any combination thereof, and a halogen containing moiety. In some embodiments, the composition comprises at least about 18 weight % of salicylic acid, ester thereof, salt thereof, or any combination thereof, wherein the weight % of salicylic acid is based on the total weight % of the composition.

One embodiment of the current disclosure is a method of treatment of a skin infection comprising administering to a subject in need thereof a therapeutically-effective amount of a pharmaceutical composition comprising: a unit dose of at least about 18 weight % of a keratolytic agent, wherein the weight % of the keratolytic agent is based on a total weight % of the composition, a molecule comprising an oxo group and an acidic group, ester thereof, salt thereof, or any combination thereof, and a halogen containing moiety.

One embodiment of the current disclosure is a pharmaceutical composition, comprising: a weight % of salicylic acid, ester thereof, salt thereof, or any combination thereof, from about 25% to about 30%, wherein the weight % of salicylic acid is based on a total weight % of the composition, a weight % of ethyl pyruvate, ester thereof, salt thereof, or any combination thereof, from about 10% to about 20%, wherein the weight % of ethyl pyruvate is based on a total weight % of the composition, and a weight % of polyvinylpyrrolidone-iodine from about 0.1% to about 1%, wherein the weight % of polyvinylpyrrolidone-iodine is based on a total weight % of the composition.

One embodiment of the current disclosure is a method of making a pharmaceutical composition, comprising combining: a weight % of salicylic acid, ester thereof, salt thereof, or any combination thereof, from about 25% to about 30%, wherein the weight % of salicylic acid is based on a total weight % of the composition, a molecule comprising an oxo group and an acidic group, ester thereof, salt thereof, or any combination thereof, and a halogen containing moiety.

One embodiment of the current disclosure is a method of preventing a cancer initiated by a virus comprising applying a composition comprising: a unit dose of at least about 18 weight % of a keratolytic agent, wherein the weight % of the keratolytic agent is based on a total weight % of the composition, a molecule comprising an oxo group and an acidic group, ester thereof, salt thereof, or any combination thereof, and a halogen containing moiety.

One embodiment of the current disclosure is a method for treatment of a wart comprising administering to a subject in need thereof a therapeutically-effective amount of a composition comprising: a weight % of salicylic acid, ester thereof, salt thereof, or any combination thereof, from about 25% to about 30%, wherein the weight % of salicylic acid is based on a total weight % of the composition, a weight % of ethyl pyruvate, ester thereof, salt thereof, or any combination thereof, from about 10% to about 20%, wherein the weight % of ethyl pyruvate is based on a total weight % of the composition, and a weight % of polyvinylpyrrolidone-iodine from about 0.1% to about 1%, wherein the weight % of polyvinylpyrrolidone-iodine is based on a total weight % of the composition.

One aspect of the present disclosure provides a composition for treating skin infections, comprising: in 100 parts of the composition, 1-99 parts of a pharmaceutically acceptable excipient; 99-1 parts of a keratolytic; 99-1 parts ethyl pyruvate; and 99-1 parts povidone iodine.

One aspect of the present disclosure provides a method for treating skin infections, comprising: topically applying a composition, comprising: in 100 parts of a composition, 1-99 parts of a pharmaceutically acceptable excipient; 99-1 parts of a keratolytic; 99-1 parts ethyl pyruvate; and 99-1 parts povidone iodine, at ambient temperature, without using cryotherapy, to an infection of the skin, resulting in a higher cure rate than would be achieved if the infection were treated by topically applying a control composition having only the keratolytic and balance being the pharmaceutically acceptable excipient.

One embodiment of the current disclosure is a pharmaceutically effective composition for treatment of skin infections, comprising: in 100 parts of the composition, 1-99 parts of a pharmaceutically acceptable excipient; 99-1 parts of a keratolytic; 99-1 parts ethyl pyruvate; and 99-1 parts povidone iodine. In some aspects, the composition comprises: in 100 parts of the composition, 0-99 parts of a pharmaceutically acceptable excipient, 49.9-10 parts of a keratolytic, 50-5 parts ethyl pyruvate, and 19-0.1 parts povidone iodine. In some aspects, the composition comprises: in 100 parts of the composition, 0-99 parts of a pharmaceutically acceptable excipient, 0.4 parts to about 0.6 parts povidone iodine USP, 12.0 parts to about 18.0 parts ethyl pyruvate, and 13.6 parts to about 20.4 parts salicylic acid USP. In some aspects, the composition comprises: in 100 parts of the composition, 0-99 parts of a pharmaceutically acceptable excipient, 0.4 parts to about 0.6 parts povidone iodine USP, 12.0 parts to about 18.0 parts ethyl pyruvate, and 19.2 parts to about 28.8 parts salicylic acid USP. In some aspects, the pharmaceutically acceptable excipient includes a thickening agent, wherein the thickening agent is selected from the group consisting of nitrocellulose and hydroxypropyl Cellulose NF. In some aspects, the keratolytic is selected from the group consisting of salicylic acid, pyruvic acid, chloroacetic acid, menthol, acetic acid, ascorbic acid, calcium pantothenate and lactic acid. In some aspects, the excipient is selected from the group consisting of polyethylene (PEG), ethylene glycol (EG), polypropylene glycol (PPG), propylene glycol (PG) and diethylene glycol monosubstituted ether (DGMSE). In some aspects, the excipient is selected from the group consisting of BHT, glycerin, propylene glycol, transcutol, triethanolamine, hydroxypropyl cellulose, and combinations thereof. In some aspects, the skin infection is caused by human papillomavirus (HPV). In some aspects, the skin infection is warts (verrucae) or squamous cell papilloma. In some aspects, the skin infection is cancer. In some aspects, the cancer is selected from the group consisting of cancer of the cervix, cancer of the vulva, cancer of the vagina, cancer of the penis, cancer of the oropharynx and cancer of the anus.

One embodiment of the current disclosure is a method for treating skin infections, comprising: topically applying the pharmaceutically effective composition of claim 1 at ambient temperature to an infection of the skin for treatment period prescribed by a physician, resulting in a higher cure rate than would be achieved if the infection were treated by topically applying a control composition having only the keratolytic and balance being the pharmaceutically acceptable excipient. In some aspects, the keratolytic is selected from the group consisting of salicylic acid, pyruvic acid, chloroacetic acid, menthol, acetic acid, ascorbic acid, calcium pantothenate and lactic acid. In some aspects, the excipient is selected from the group consisting of polyethylene glycol (PEG), ethylene glycol (EG), polypropylene glycol (PPG), propylene glycol (PG) and diethylene glycol monosubstituted ether (DGMSE). In some aspects, the excipient is selected from the group consisting of BHT, glycerin, propylene glycol, transcutol, triethanolamine, hydroxypropyl cellulose, and combinations thereof. In some aspects, the skin infection is caused by Human papillomavirus (HPV). In some aspects, the skin infection is warts (verrucae) or squamous cell papilloma. In some aspects, the skin infection is cancer. In some aspects, the cancer is selected from the group consisting of cancer of the cervix, cancer of the vulva, cancer of the vagina, cancer of the penis, cancer of the oropharynx and cancer of the anus.

While preferred embodiments of the present disclosure are shown and described herein, it is not meant to limit the present disclosure in any fashion. The methods described herein are presently representative of preferred embodiments and are exemplary, and are not intended as limitations on the scope of the disclosure. Changes therein and other uses which are encompassed within the spirit of the disclosure as defined by the scope of the claims will occur to those skilled in the art.

BACKGROUND OF THE INVENTION

The present disclosure relates to compositions and methods of treatment of skin infection caused by Human papillomavirus (HPV). Specifically, the present disclosure relates to compositions and methods of treating benign papillomas, such as skin warts or squamous cell papilloma, or cancer, such as cancer of the cervix, cancer of the vulva, cancer of the vagina, cancer of the penis, cancer of the oropharynx and cancer of the anus.

A meta-analysis of topical treatment for cutaneous warts found a cure rate of 23% (5-73%) in placebo trials, 52% (0-87%) in salicylic acid trials, 49% (0-69%) in cryotherapy trials, 54% (45-75%) in aggressive cryotherapy trials and 58% (38-78%) in the combined cryotherapy and salicylic acid trials. There continues to be a need for improved compositions and methods for treating skin infection caused by Human papillomavirus (HPV).

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 depicts a flow diagram of a method for treating an infection caused by HPV, in accordance to embodiments of the present disclosure.

DETAILED DESCRIPTION OF THE INVENTION

Pharmaceutical Compositions

Figure 2:
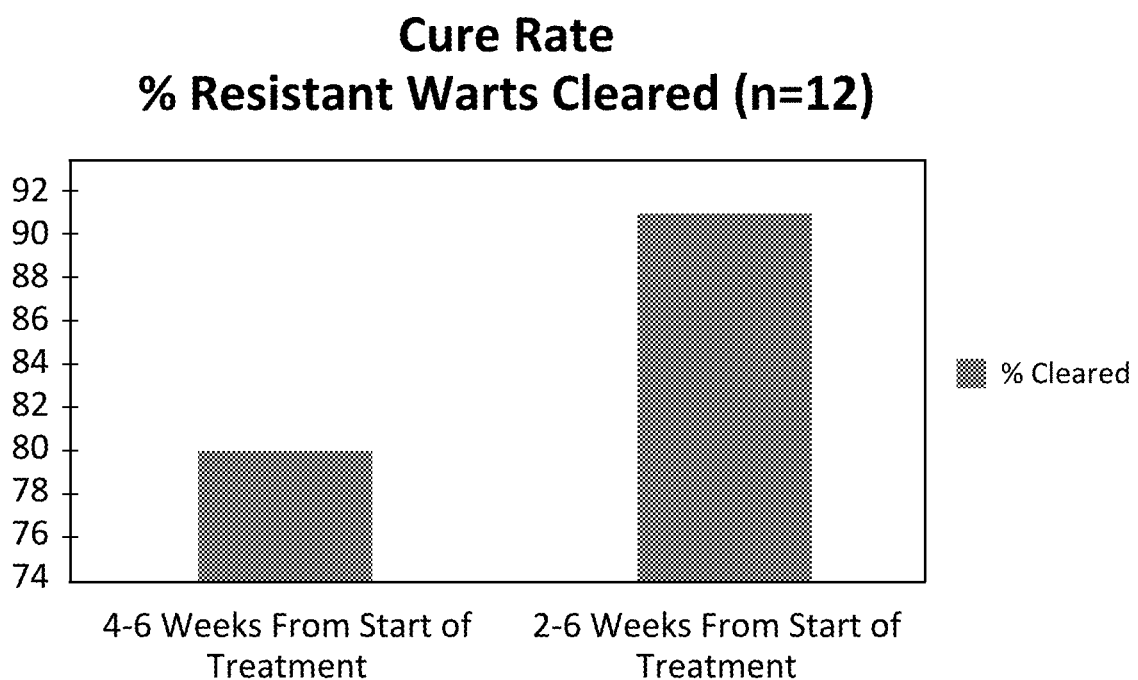
FIG. 2 depicts a chart illustrating results from topical treatment of resistant wart patients in accordance with embodiments of the present disclosure.

The term "salt" refers to salts derived from a variety of organic and inorganic counter ions well known in the art. Acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the base addition salt is chosen from ammonium, potassium, sodium, calcium, and magnesium salts.

The term "subject" includes, but is not limited to, humans of any age group, e.g., a pediatric subject (e.g., infant, child or adolescent) or adult subject (e.g., young adult, middle-aged adult or senior adult) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The methods described herein can be useful in both human therapeutics and veterinary applications. In some embodiments, the patient is a mammal, and in some embodiments, the patient is human. In some embodiments, a composition of the current disclosure is administered to a subject in need thereof.

In some embodiments, a composition of the current disclosure is administered to an infected cell. In some embodiments, a composition of the current disclosure is administered to an infected skin cell.

The term "therapeutically-effective amount" refers to that amount of compound that is sufficient to effect treatment, when administered to a mammal in need of such treatment. The therapeutically-effective amount will vary depending upon the subject and disease condition being treated, the weight and age of the subject, the severity of the disease condition, the manner of administration and the like, which can readily be determined by one of ordinary skill in the art.

The compounds of the disclosure, or their pharmaceutically acceptable salts, may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present disclosure is meant to include all such possible isomers, as well as their racemic and optically pure forms.

The term "pharmaceutically acceptable excipient" includes solvents, dispersion media, coatings, antibacterial and antifungal agents, isotonic and absorption delaying agents. Except insofar as any conventional media or agent is incompatible with the active ingredient, its use in the therapeutic compositions of the disclosure is contemplated. Supplementary active ingredients can also be incorporated into the compositions.

The term "treating" or "treatment" may include preventing a disease-state from occurring in a mammal, inhibiting a disease state, and relieving the disease state. Treating also may include the amelioration of a symptom of a disease (e.g., lessen the pain or discomfort), wherein such amelioration may or may not be directly affecting the disease (e.g., cause, transmission, expression, etc.).

As used herein, unless otherwise defined, the term "resistant warts" or "resistant warts patients" refers to warts or patients with warts that do not clear readily. For example, a wart may not clear when topically treated with a composition.

As used herein, unless otherwise defined, the term "cure" may mean being free of a medical condition. A "cure rate" may mean no visible symptoms for non-cancer diseases, as a percent of the originally infected population. "Cure" for cancer may be defined as being symptom free for more than 5 years.

The term "plantar wart" may also be known as verruca, myrmecia and *verruca plantaris*. Treatment for plantar warts may be recommended to lessen symptoms (which may include pain), decrease duration, and reduce transmission.

As used herein, unless otherwise defined, the term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance, and bioavailability.

As used herein, unless otherwise defined, the term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance, and bioavailability.

As used herein, unless otherwise defined, the terms "pharmaceutically effective amount", "pharmaceutically effective dose" or "pharmaceutically effective relief" is defined as an amount or dose that results in eradication of the wart, so that may not detectable by a physician. A therapeutically effective dose is an amount or dose that is effective for treating or preventing the disease or condition.

A composition of the current disclosure may comprise a keratolytic agent. In some embodiments, a keratolytic agent causes softening, shedding, or the combination thereof, of the outer layer of the skin. A keratolytic agent may be a peeling agent. In some embodiments, a keratolytic agent can be salicylic acid, pyruvic acid, chloroacetic acid, menthol, acetic acid, ascorbic acid, calcium pantothenate or lactic acid. In some embodiments, a keratolytic agent of a composition of the current disclosure is salicylic acid.

A composition of the current disclosure may comprise a molecule comprising an oxo group and an acidic group, or ester or salt thereof. A composition may comprise a molecule comprising an oxo group and an acidic group, wherein the molecule comprises a pyruvate group. A composition of may comprise a molecule comprising an oxo group and an acidic group, wherein the molecule can be methyl pyruvate, ethyl pyruvate, propyl pyruvate, or pyruvic acid. A composition of the current disclosure may comprise a molecule comprising an oxo group and an acidic group, wherein the molecule is ethyl pyruvate.

A composition of the current disclosure may comprise a halogen containing moiety. A composition may comprise fluorine, bromine, iodine, chlorine, or combinations thereof. A composition may comprise iodine. A composition may comprise a cation, wherein the cation can be selected from the group consisting of hydrogen cation, ammonium cation, and polyvinylpyrrolidone cation. A composition of the current disclosure may comprise polyvinylpyrrolidone-iodine.

In some embodiments, the amount of a compound in a composition can be expressed by weight %, wherein the weight % of the compound is based on a total weight % of the composition.

In some embodiments, a compound can be present in a composition in about 0.1 weight %, 0.2 weight %, 0.3 weight %, 0.4 weight %, 0.5 weight %, 0.6 weight %, 0.7 weight %, 0.8 weight %, 0.9 weight %, 1 weight %, 2 weight %, 3 weight %, 4 weight %, 5 weight %, 6 weight %, 7 weight %, 8 weight %, 9 weight %, 10 weight %, 11 weight %, 12 weight %, 13 weight %, 14 weight %, 15 weight %, 16 weight %, 17 weight %, 18 weight %, 19 weight %, 20 weight %, 21 weight %, 22 weight %, 23 weight %, 24 weight %, 25 weight %, 26 weight %, 27 weight %, 28 weight %, 29 weight %, 30 weight %, 35 weight %, 40 weight %, 50 weight %, 60 weight %, 70 weight %, 80 weight %, 90 weight %, or 95 weight %, wherein the weight % of the compound is based on a total weight % of the composition. In some embodiments, a compound is present in a composition in greater than about 0.1 weight %, 0.2 weight %, 0.3 weight %, 0.4 weight %, 0.5 weight %, 0.6 weight %, 0.7 weight %, 0.8 weight %, 0.9 weight %, 1 weight %, 2 weight %, 3 weight %, 4 weight %, 5 weight %, 6 weight %, 7 weight %, 8 weight %, 9 weight %, 10 weight %, 11 weight %, 12 weight %, 13 weight %, 14 weight %, 15 weight %, 16 weight %, 17 weight %, 18 weight %, 19 weight %, 20 weight %, 21 weight %, 22 weight %, 23 weight %, 24 weight %, 25 weight %, 26 weight %, 27 weight %, 28 weight %, 29 weight %, 30 weight %, 35 weight %, 40 weight %, 50 weight %, 60 weight %, 70 weight %, 80 weight %, 90 weight %, or 95 weight %, wherein the weight % of the compound is based on a total weight % of the composition.

In some embodiments, a compound is present in a composition in a positive amount and less than about 0.1 weight %, 0.2 weight %, 0.3 weight %, 0.4 weight %, 0.5 weight %, 0.6 weight %, 0.7 weight %, 0.8 weight %, 0.9 weight %, 1 weight %, 2 weight %, 3 weight %, 4 weight %, 5 weight %, 6 weight %, 7 weight %, 8 weight %, 9 weight %, 10 weight %, 11 weight %, 12 weight %, 13 weight %, 14 weight %, 15 weight %, 16 weight %, 17 weight %, 18 weight %, 19 weight %, 20 weight %, 21 weight %, 22 weight %, 23 weight %, 24 weight %, 25 weight %, 26 weight %, 27 weight %, 28 weight %, 29 weight %, 30 weight %, 35 weight %, 40 weight %, 50 weight %, 60 weight %, 70 weight %, 80 weight %, 90 weight %, or 95 weight %, wherein the weight % of the compound is based on a total weight % of the composition.

In some embodiments, the amount of a keratolytic agent in a composition is expressed by weight %, wherein the weight % of the keratolytic agent is based on a total weight % of the composition. In some embodiments, the amount of a keratolytic agent in a composition is greater than about 18 weight %, 19 weight %, 20 weight %, 21 weight %, 22 weight %, 23 weight %, 24 weight %, 25 weight %, 26 weight %, 27 weight %, 28 weight %, 29 weight %, 30 weight %, 35 weight %, 40 weight %, or 50 weight %, wherein the weight % of the keratolytic agent is based on a total weight % of the composition. In some embodiments, the amount of a keratolytic agent in a composition is greater than about 18 weight %. In some embodiments, the amount of a keratolytic agent in a composition is from about 25 weight % to about 30 weight %. In some embodiments, the amount of a keratolytic agent in a composition is about 28 weight %. In some embodiments, a keratolytic agent is salicylic acid. In some embodiments, the amount of salicylic acid in a composition is greater than about 18 weight %, wherein the weight % of salicylic is based on a total weight % of the composition. In some embodiments, the amount of salicylic acid in a composition is from about 25 weight % to about 30 weight %. In some embodiments, the amount of salicylic acid in a composition is about 28 weight %.

In some embodiments, the amount of ethyl pyruvate in a composition is expressed by weight %, wherein the weight % of the ethyl pyruvate is based on a weight % of the composition. In some embodiments, the amount of a ethyl pyruvate in a composition is about 10 weight %, 11 weight %, 12 weight %, 13 weight %, 14 weight %, 15 weight %, 16 weight %, 17 weight %, 18 weight %, 19 weight %, or 20 weight %, wherein the weight % of the ethyl pyruvate is based on a weight % of the composition. In some embodiments, the amount of ethyl pyruvate in a composition is from about 10 weight % to about 20 weight %. In some embodiments, the amount of ethyl pyruvate in a composition is about 12 weight %.

In some embodiments, the amount of polyvinylpyrrolidone-iodine in a composition is expressed by weight %, wherein the weight % of polyvinylpyrrolidone-iodine is based on a weight % of the composition. In some embodiments, the amount of polyvinylpyrrolidone-iodine in a composition is about 0.1 weight %, 0.2 weight %, 0.3 weight %, 0.4 weight %, 0.5 weight %, 0.6 weight %, 0.7 weight %, 0.8 weight %, 0.9 weight %, or 1 weight %, wherein the weight % of polyvinylpyrrolidone-iodine is based on a weight % of the composition. In some embodiments, the amount of polyvinylpyrrolidone-iodine in a composition is from about 0.1 weight % to about 1 weight %. In some embodiments, the amount of polyvinylpyrrolidone-iodine in a composition is about 0.5 weight %.

In some embodiments, the ratio of ethyl pyruvate to salicylic acid in a composition is about 1:1, 1:2, 1:3, 1:4, 1:5, 1:6, 1:7, 1:8, 1:9, 1:10, 2:3, 2:5, 2:7, 2:9, 2:11, 2:13, 2:15, 2:17, 2:19, 3:5, 3:7, 3:8, 3:10, 3:11, 3:13, 3:14, 3:16, 3:17, 3:19, 4:5, 4:7, 4:9, 4:11, 4:13, 4:15, 4:17, 4:19, 5:6, 5:8, 5:9, 5:11, 5:12, 5:13, 5:14, 5:16, 5:17, 5:18, 5:19, 6:7, 6:11, 6:13, 6:17, 6:19, 7:8, 7:9, 7:10, 7:11, 7:12, 7:13, 7:15, 7:16, 7:18, 7:19, 8:9, 8:11, 8:13, 8:15, 8:17, 8:19, 9:10, 9:11, 9:13, 9:14, 9:16, 9:17, 9:19, 10:11, 10:13, 10:17, 10:19, 11:12, 11:13, 11:14, 11:15, 11:16, 11:17, 11:18, 11:19, 11:20, 12:13, 12:17, 12:19, 13:14, 13:15, 13:16, 13:17, 13:18, 13:19, 13:20, 14:15, 14:17, 14:19, 15:16, 15:17, 15:19, 16:17, 16:19, 17:18, 17:19, 17:20, 18:19, or 19:20, wherein the ratio is based on a ratio of weight % of ethyl pyruvate to salicylic acid. In some embodiments, the ratio of ethyl pyruvate to salicylic acid in a composition is about 1:1, 1:2, 1:3, 1:4, or 1:5, wherein the ratio is based on a ratio of weight % of ethyl pyruvate to salicylic acid. In some embodiments, the ratio of ethyl pyruvate to salicylic acid in a composition is about 1:1, wherein the ratio is based on a ratio of weight % of ethyl pyruvate to salicylic acid.

In some embodiments, the ratio of polyvinylpyrrolidone-iodine to salicylic acid in a composition is about 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:120, or 1:150, wherein the ratio is based on a ratio of weight % of polyvinylpyrrolidone-iodine to salicylic acid. In some embodiments, the ratio of polyvinylpyrrolidone-iodine to salicylic acid in a composition is about 1:90. In some embodiments, the ratio of polyvinylpyrrolidone-iodine to salicylic acid in a composition is about 1:120.

In some embodiments, the ratio of polyvinylpyrrolidone-iodine to ethyl pyruvate in a composition is about 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:120, or 1:150, wherein the ratio is based on a ratio of weight % of polyvinylpyrrolidone-iodine to ethyl pyruvate. In some embodiments, the ratio of polyvinylpyrrolidone-iodine to ethyl pyruvate in a composition is about 1:90, wherein the ratio is based on a ratio of weight %. In some embodiments, the ratio of polyvinylpyrrolidone-iodine to ethyl pyruvate in a composition is about 1:120, wherein the ratio is based on a ratio of weight %.

In some embodiments, the pharmaceutical composition administered to a patient is in a unit dose, wherein the unit dose is in an amount from about 0.0001 g-500 g, 0.001 g-250 g, 0.01 g-100 g, 0.1 g-50 g, or 1 g-10 g. In some embodiments, the unit dose is about or more than about 0.0001 g, 0.001 g, 0.01 g, 0.1, 0.5 g, 1 g, 2 g, 3 g, 4 g, 5 g, 6 g, 7 g, 8 g, 9 g, 10 g, 15 g, 20 g, 25 g, 50 g, 100 g, 200 g, 250 g, 300 g, 350 g, 400 g, 450 g, 500 g, or more. In some embodiments, the unit dose is an amount from about 0.001 g-100 g. In some embodiments, the unit dose is an amount from about 0.1 g-10 g. In some embodiments, the unit dose is an amount from about 0.1 g-5 g.

In some embodiments, the composition can be provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. In some embodiments, a unit dose may be administered once a day. In some embodiments, a unit dose may be administered twice a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer.

The unit doses can be administered simultaneously or sequentially. The composition can be administered for an extended treatment period. The treatment period can be about 1 minute, 1 hour, 12 hours, 1 day, 2 days, 3 days, 7 days, 14 days, 28 days, 1 month, 2 months, 3 months, 6 months, or 1 year. In some embodiments, the treatment period may be until symptoms recede. In some embodiments, the composition is administered for a period of at least 1 minute. In some embodiments, the composition is administered for a period of at least 1 hour.

In some embodiments, a composition of the current disclosure is administered at least once a day for a period of at least one week. In some embodiments, a composition of the current disclosure is administered at least twice a day for a period of at least one week. In some embodiments, a composition of the current disclosure is administered at least once a day for a period of at least one month.

In some embodiments, a composition of the current disclosure can be contacted with infected skin at least once a day for a period of at least one week. In some embodiments, a composition of the current disclosure can be contacted with infected skin at least twice a day for a period of at least one week. In some embodiments, a composition of the current disclosure can be contacted with infected skin at least once a day for a period of at least one month.

In some embodiments, the pharmaceutical composition administered to a patient comprises a keratolytic agent, wherein the keratolytic agent is present in an amount from about 0.001-100 g. In some embodiments, the pharmaceutical composition administered to a patient comprises a keratolytic agent, wherein the keratolytic agent is present in an amount from about 0.1-10 g. In some embodiments, a composition of the current disclosure can be administered, wherein the administration can be selected from the group consisting of contacting, applying, administering, lathering, rubbing, dispensing, dispersing, and distributing.

In some embodiments, a therapeutically-effective amount of a composition of the current disclosure can sufficiently provide any one or more of the therapeutic effects described herein. As an example, the therapeutically-effective amount can be in the range of about 0.0001-1000 mg/kg body weight, 0.001-500 mg/kg body weight, 0.01-100 mg/kg body weight, 0.01-30 mg/kg body weight, 0.1-200 mg/kg body weight, 3-200 mg/kg body weight, 5-500 mg/kg body weight, 10-100 mg/kg body weight, 10-1000 mg/kg body weight, 50-200 mg/kg body weight, 100-1000 mg/kg body weight, 200-500 mg/kg body weight, 250-350 mg/kg body weight, or 300-600 mg/kg body weight of a composition of the current disclosure. In some embodiments, the therapeutic amount can be about or more than about 0.0001 mg/kg body weight, 0.001 mg/kg body weight, 0.0.1 mg/kg body weight, 0.1 mg/kg body weight, 0.5 mg/kg body weight, 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 15 mg/kg body weight, 20 mg/kg body weight, 25 mg/kg body weight, 50 mg/kg body weight, 100 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 600 mg/kg body weight, 800 mg/kg body weight, 1000 mg/kg body weight, or more of a composition of the current disclosure. In some embodiments, the effective amount is at least about 0.001 mg/kg body weight of a composition of the current disclosure. In some embodiments, the effective amount is an amount between about 0.01-30 mg/kg body weight of a composition of the current disclosure. In some embodiments, the therapeutic amount can be an amount between about 30-150 mg/kg body weight of a composition of the current disclosure.

The amount of composition administered will be dependent on the mammal being treated, the severity of the disorder or condition, the rate of administration, the disposition of the compound and the discretion of the prescribing physician. However, an effective dosage may be in the range of about 0.001 to about 10,000 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day.

The term "about" when referring to a number or a numerical range means that the number or numerical range referred to is an approximation within experimental variability (or within statistical experimental error), and thus the number or numerical range may vary from, for example, 1% to 10% of the stated number or numerical range.

In some embodiments, the disclosure provides a method for administration of a composition of the current disclosure to a subject in need thereof. In some embodiments, a pharmaceutical composition comprising a compound of the current disclosure may be administered to a subject in need thereof.

Subjects may be monitored for therapeutic effectiveness using assays and methods suitable for the condition being treated, which assays will be familiar to those having ordinary skill in the art and are described herein. Pharmacokinetics of a compound of the current disclosure that is administered to a subject may be monitored by determining the level of the compound in a biological fluid, for example, in the blood, blood fraction (e.g., serum), and/or in the urine, and/or other biological sample or biological tissue from the subject. Any method practiced in the art and described herein to detect the compound may be used to measure the level of the compound during a treatment course.

In some embodiments, an infection can cause a symptom. Symptoms can include, but are not limited to, redness, tenderness, swelling, warmth of the infected area, a wart, a rash, a discolored patch of skin, scaling, cracking, soreness, maceration, pimples, pustules, lesions, or combinations thereof. In some embodiments, a symptom can be a wart.

A composition of the current disclosure may be used to treat a symptom of a skin infection. In some embodiments, the method reduces the diameter of a wart by at least about 5%, 10%, 20%, 30%, 40%, 50%, 60%, 70%, 80%, 90%, or more. In some embodiments, the method reduces the diameter of a wart by at least 50%. In some embodiments, the method reduces the mass of a wart by at least about 5%, 10%, 20%, 30%, 40%, 50%, 60%, 70%, 80%, 90%, or more. In some embodiments, the method reduces the mass of a wart by at least 10%. In some embodiments, the method reduces the volume of a wart by at least about 5%, 10%, 20%, 30%, 40%, 50%, 60%, 70%, 80%, 90%, or more. In some embodiments, the method reduces the volume of a wart by at least 10%. In some embodiments, a method of the current disclosure is a method for treatment of a wart comprising administering to a subject in need thereof a therapeutically-effective amount of a composition comprising: a weight % of salicylic acid, or a salt thereof, from about 25% to about 30%, wherein the weight % of salicylic acid is based on a weight % of the composition, a weight % of ethyl pyruvate, or a salt thereof, from about 10% to about 20%, wherein the weight % of ethyl pyruvate is based on a weight % of the composition, and a weight % of polyvinylpyrrolidone-iodine from about 0.1% to about 1%, wherein the weight % of polyvinylpyrrolidone-iodine is based on a weight % of the composition.

A composition of the current disclosure may be used in a method, wherein the method induces a lower amount of a symptom compared to other compositions, wherein these other compositions comprise an ingredient selected from the group consisting of 5-fluorouracil, dinitrochlorobenzene, bleomycin, cantharidin, and any combination thereof. A composition of the current disclosure may induce a lower amount of a symptom by at least about 5%, 10%, 20%, 30%, 40%, 50%, 60%, 70%, 80%, 90%, or more. In some embodiments, a method of the current disclosure induces lower than about 50% of a symptom compared to a method employing a composition comprising an ingredient selected from the group consisting of 5-fluorouracil, dinitrochlorobenzene, bleomycin, cantharidin, and any combination thereof.

A composition of the current disclosure may be used in a method, wherein the method exhibits greater efficacy compared to other compositions, wherein these other compositions comprise an ingredient selected from the group consisting of 5-fluorouracil, dinitrochlorobenzene, bleomycin, cantharidin, and any combination thereof. A composition of the current disclosure may exhibit greater efficacy compared to other compositions by at least about 5%, 10%, 20%, 30%, 40%, 50%, 60%, 70%, 80%, 90%, or more. A composition of the current disclosure may exhibit greater efficacy compared to other compositions by at least about 10%. A composition of the current disclosure may exhibit greater efficacy compared to other compositions by at least about 50%. A composition of the current disclosure may exhibit greater efficacy compared to other compositions by at least about 75%.

A composition of the current disclosure may be used in a method to treat skin infections that are resistant to other methods that employ compositions that comprise an ingredient selected from the group consisting of 5-fluorouracil, dinitrochlorobenzene, bleomycin, cantharidin, and any combination thereof. In some embodiments, a subject had been previously diagnosed with a skin infection prior to administration of a composition of the current disclosure.

Combination Therapy

In some embodiments, pharmaceutical compositions disclosed herein can be used in combination therapy with other therapeutic agents. The pharmaceutical compositions disclosed herein and the therapeutic agent can act additively or synergistically. In some embodiments, pharmaceutical compositions disclosed herein are administered concurrently with the administration of another therapeutic agent. In some embodiments, pharmaceutical compositions disclosed herein are administered prior or subsequent to administration of other therapeutic agents. Other therapeutic agents may include, but are not limited to, 5-fluorouracil, dinitrochlorobenzene, bleomycin, cantharidin, or any combination thereof.

In some embodiments, pharmaceutical compositions disclosed herein can be used in combination therapy with additional treatments. The pharmaceutical compositions disclosed herein and the additional treatments can act additively or synergistically. In some embodiments, pharmaceutical compositions disclosed herein are administered concurrently with the additional treatments. In some embodiments, pharmaceutical compositions disclosed herein are administered prior or subsequent to additional treatments. Additional treatments may include, but are not limited to, cryotherapy, electrosurgery, excision, laser treatment, surgery, immunotherapy, or any combination thereof.

In some embodiments, pharmaceutical compositions disclosed herein can be used in combination therapy with an additional active agent. The additional active agent may be an antiviral drug, an anticancer drug, an antibacterial drug, or any combinations thereof. In some embodiments, the additional active agent is an antiviral drug. In some embodiments, the additional active agent is 5-fluorouracil, dinitrochlorobenzene, bleomycin, cantharidin, minocycline, doxycycline, tetracycline, erythromycin, metronidazole, sulfacetamide, clindamycin, sulfacetamide, or any combination thereof.

In one embodiment, the composition for treating skin infections advantageously comprises in 100 parts of the composition, 0-99 parts of a pharmaceutically acceptable excipient, 49.9-10 parts of a keratolytic, 50-5 parts ethyl pyruvate, and 19-0.1 parts povidone iodine.

In one embodiment, the composition for treating skin infections advantageously comprises in 100 parts of the composition, 0-99 parts of a pharmaceutically acceptable excipient, 0.4 parts to about 0.6 parts povidone iodine USP, 12.0 parts to about 18.0 parts ethyl pyruvate, and 19.2 parts to about 28.8 parts salicylic acid USP.

In some embodiments, the pharmaceutical composition of the current disclosure comprises an excipient. Some examples of excipients include starches, gum acacia, calcium phosphate, alginates, tragacanth, gelatin, calcium silicate, microcrystalline cellulose, PEG, nitrocellulose, hydroxypropyl Cellulose NF, polyvinylpyrrolidone, cellulose, water, sterile saline, syrup, and methyl cellulose, lubricating agents such as talc, magnesium stearate, and mineral oil, wetting agents, emulsifying and suspending agents, preserving agents such as methyl- and propylhydroxy-benzoates; sweetening agents, flavoring agents such as lactose, dextrose, sucrose, sorbitol, mannitol, and scented agents, such as cinnamon, olive oil, menthol, saffron, citrus.

In some embodiments, the pharmaceutical composition of the current disclosure comprises an excipient, wherein the excipient is selected from ethyl alcohol, camphor, castor oil, collodion, ethyl ether, ethylcullulose, hypophosphorous acid, menthol, and polysorbate 80.

In some embodiments, an excipient may be a thickening agent. In some embodiments, a composition of the current disclosure comprises a thickening agent, wherein the thickening agent may be selected from the group consisting of polyethylene glycol, polyacrylic acid, vegetable gums, petroleum jelly, guar gum, sodium chloride, nitrocellulose, hydroxypropyl cellulose, and any combination thereof. In some embodiments, a thickening agent may be selected from the group consisting of nitrocellulose, hydroxypropyl cellulose, and any combination thereof. In some embodiments, a thickening agent may be nitrocellulose. In some embodiments, a thickening agent is hydroxypropyl Cellulose NF. In some embodiments, the excipient may be selected from the group consisting of water, polyethylene glycol, ethylene glycol, polypropylene glycol, propylene glycol, 2-(2-ethoxyethoxy)ethanol, butylated hydroxytoluene, glycerin, 2-(2-ethoxyethoxy)ethanol, triethanolamine, Vitamin E, mineral oil, and dimethyl sulfoxide, gelatin, calcium silicate, and hydroxypropyl cellulose. In some embodiments, the excipient may be polyethylene (PEG), ethylene glycol (EG), polypropylene glycol (PPG), propylene glycol (PG) or diethylene glycol monosubstituted ether (DGMSE). In some embodiments, the excipient may be glycerin, propylene glycol, transcutol, triethanolamine, hydroxypropyl cellulose, or combinations thereof. In some embodiments, the excipient may be polyethylene glycol, ethylene glycol, polypropylene glycol, propylene glycol, or diethylene glycol monosubstituted ether. A pharmaceutically acceptable excipient may be used to promote solubilization of the components of the pharmaceutically effective composition.

Composition of the current disclosure may be formulated for rapid, sustained, delayed release, or combinations thereof.

FIG. 1 depicts a method 100 for treating skin infections. The method 100 comprises a step 105: topically applying to an infection of the skin for treatment period prescribed by a physician, at ambient temperature, without using cryotherapy, a composition for treating skin infections, comprising: in 100 parts of the composition, 1-99 parts of a pharmaceutically acceptable excipient; 99-1 parts of a keratolytic; 99-1 parts ethyl pyruvate; and 99-1 parts povidone iodine, resulting in a higher cure rate than would be achieved if the infection were treated by topically applying a control composition having only the keratolytic and balance being the pharmaceutically acceptable excipient.

Ethyl alcohol may be used to dissolve components of the pharmaceutically effective composition for treating infections caused by HPV. Alcohols, such as isopropyl alcohol, methyl alcohol, propyl alcohol, ethyl alcohol, cetyl alcohol, stearyl alcohol, cetearyl alcohol, and lanolin alcohol, may be used for dissolving or taking up the components in the pharmaceutically effective composition for treating infections caused by HPV. Alternatively, for example, for topical formulations, pharmaceutically acceptable excipients may comprise solvents, emollients, humectants, preservatives, emulsifiers, and pH adjusting agents. Suitable solvents include acetone, glycols, polyurethanes, and others known in the art. Suitable emollients include mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH adjusting agents include hydrochloric acid, phosphoric acid, diethanolamine, triethanolamine, sodium hydroxide, monobasic sodium phosphate, dibasic sodium phosphate, and others known in the art. Alternatively, pH adjusting agents include, from about 1 percent by weight to about 15 percent by weight, acetic acid, citric acid, pyruvic or lactic acid. Suitable preservatives include butylated hydroxytoluene NF, benzyl alcohol, sodium benzoate, parabens, and others known in the art.

Polyethylene glycol (PEG), ethylene glycol (EG), polypropylene glycol (PPG), propylene glycol (PG) and the diethylene glycol monosubstituted ether (DGMSE) can be pharmaceutically acceptable excipients. DGMSE may be known as 2-(2-ethoxyethoxy)ethanol, Carbitol, Carbitolcellosolve, Transcutol, Dioxitol, Poly-solv DE, and Dowanol DE. Not wishing to be bound by theory, polyethylene glycol (PEG), ethylene glycol (EG), polypropylene glycol (PPG), propylene glycol (PG) and the diethylene glycol monosubstituted ether (DGMSE) may hydrogen bond to trace nucleophiles that may be contaminants in the pharmaceutically acceptable excipients, thereby reducing the nucleophilic strength of the trace nucleophiles. This may reduce the chance that ethyl pyruvate may decompose by undergoing disadvantageous nucleophilic attack by the trace nucleophiles. Therefore diethylene glycol monosubstituted ether (DGMSE) or silicones such as dimethicone or cyclomethicone may be useful as pharmaceutically acceptable excipients.

In one embodiment, patients topically treated with the pharmaceutically effective composition for treating infections caused by HPV compounded into a polypropylene glycol (PPG, molecular weight from about 300 to about 2500), propylene glycol (PG,), polyethyleneglycol (PEG, molecular weight from about 100 to about 1000) or ethylene glycol ointment or cream showed very little evidence of any systemic toxicities.

Hydroxypropyl cellulose, hydroxyethyl cellulose and hydroxymethyl cellulose are gelling and thickening agents derived from cellulose. Hydroxypropyl cellulose may be Hydroxypropylcellulose NF 1500 CPS. It may be used in cosmetics, cleaning solutions, and other household products. Hydroxypropyl cellulose, hydroxyethyl cellulose and hydroxymethyl cellulose can be used to solubilize hydrophobic and hydrophilic components in a composition.

Formulations

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diasteroisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

When employed as pharmaceuticals, the compounds described herein can be administered in the form of pharmaceutical compositions. This disclosure therefore provides pharmaceutical compositions which contain active ingredients or a pharmaceutically acceptable salt thereof and one or more pharmaceutically acceptable excipients, carriers, diluents, permeation enhancers, solubilizers or adjuvants. Compositions of the current disclosure may be administered alone or in combination with other therapeutic agents (e.g., vasoconstrictors, anti-inflammatory agents, antibiotics, other monobinding anesthetic bases and salts, counter-irritants), carriers, adjuvants, permeation enhancers, and the like. Pharmaceutically acceptable salts of the active agents (e.g., acid addition salts) may be prepared using standard procedures known to those skilled in the art.

Compositions of the current disclosure may be administered by any of the accepted modes of administration of agents having similar utilities, for example, by oral, topical, intradermal, intravenous, subcutaneous, intramuscular, intra-articular, intraspinal or spinal, epidural, rectal, vaginal, or transdermal/transmucosal routes. The most suitable route will depend on the nature and severity of the condition being treated. Subcutaneous, intradermal and percutaneous injections can be routes for the compounds of this disclosure. In making the compositions of this disclosure, the active ingredient can be diluted by an excipient. Some examples of suitable excipients include mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. Physiological saline may be used. Compositions of the current disclosure may be sterile. In another embodiment, for treatment of an ophthalmological condition or disease, a liquid pharmaceutical composition may be applied to the eye in the form of eye drops. A liquid pharmaceutical composition may be delivered orally.

Compositions of the current disclosure can be in the form of emulsions, creams, jelly, solutions, ointments, or combinations thereof. A composition may be semisolid.

Compositions of the current disclosure can be administered topically to non-ocular mucous membranes, such as for example oral, otic, nasal, respiratory, pharyngeal, tracheal, esophageal, urethral, or vaginal membranes. Formulations containing at least one compound of the disclosure useful for such membranes may be, for example, solutions, sprays, suspensions, gels, creams or ointments.

A composition of the current disclosure may be formulated into a topical solution, a lotion, a cream, an ointment, a gel, a foam, a patch, a powder, onto a sponge, a paste, a tincture, or any combination thereof. A composition of the current disclosure may be formulated into a cream, an ointment, or a gel. A composition of the current disclosure may be formulated into a gel. A composition of the current disclosure may be homogenous. A composition of the current disclosure may be heterogeneous.

Compatible and pharmaceutically acceptable carriers, which may be used in this disclosure, comprise e.g. an aqueous solution, such as saline solutions, oil solutions or ointments. Formulations for ocular use may also contain compatible and pharmaceutically acceptable excipients, such as preservatives, surfactants, stabilizing agents, antibacterial agents, buffering agents and agents such as for example polymers to adjust viscosity, vasoconstrictors, antihistaminic agents or anti-inflammatory agents. Formulations may be manufactured in different dosage units, suitable for ocular administration. The concentration of active compound in a formulation for use on non-ocular mucous membranes can be from about 0.01% to 20% by weight.

Injectable solutions may contain a vasoconstrictor (e.g. epinephrine or vasopressin); a solution for infusion or regional anesthesia may contain glucose or dextrose, a gel for urogenital topical procedures may contain thickening agents (e.g. hydroxypropylmethylcellulose); a preparation for topical or dermal application may contain penetration promoting agents (e.g. hydroxypolyethoxydodecane, DMSO, DMAC); sprays for topical anesthesia of the mouth and oropharynx may contain saccharin and alcohol, ointments for accessible mucous membranes may contain a lubricant. Compositions of the current disclosure can also be administered together with other membrane stabilizers (local anesthetics), for example to form eutectic mixtures. The compositions of the disclosure can also be administered together with other therapeutically active compounds, such as capsaicin, vaso-active compounds, anti-inflammatory agents, or combinations thereof.

In some embodiments, the area of skin around an infected skin cell is prepared before administration of a composition of the current disclosure. Preparation of the area of skin around an infected skin cell may include washing, drying, dressing with an absorbent material, dressing with an adhesive bandage, contacting with ice, contacting with a warm or hot cloth, or combinations thereof. In some embodiments, the area of skin around an infected skin cell is washed and dried before administration of a composition of the current disclosure. In some embodiments, an adhesive bandage is applied to an area of skin around an infected skin cell.

For oral formulations, at least one of the compounds described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in a pharmaceutical composition may be formulated for oral delivery with a flavoring agent, e.g., in a liquid, solid or semi-solid formulation and/or with an enteric coating.

A pharmaceutical composition may be formulated for sustained or slow release (also called timed release or controlled release). Such compositions may generally be prepared using known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations may be biocompatible, and may also be biodegradable. The formulation may provide a relatively constant level of active component release. Non-limiting examples of excipients include water, alcohol, glycerol, chitosan, alginate, chondroitin, Vitamin E, mineral oil, and dimethyl sulfoxide. The amount of active compound contained within a sustained release formulation depends upon the site of implantation, the rate and expected duration of release, and the nature of the condition, disease or disorder to be treated or prevented.

Compositions of the current disclosure may be solubilized and encapsulated, for example, in a liposome or a biodegradable polymer, or used in the form of microcrystals coated with an appropriate nontoxic lipid.

The compositions may be formulated to provide for drug latentiation by the conversion of hydrophilic drugs into lipid-soluble drugs. Latentiation may be achieved through blocking of the hydroxyl, carbonyl, sulfate, or primary amine groups present on a compound to render the compound more lipid soluble and amenable to transportation across tissue barriers.

Compositions of the disclosure may be formulated as a spray. Compositions may include solutions and suspensions in pharmaceutically acceptable, aqueous or organic solvents, or mixtures thereof, and powders. The liquid or solid compositions may contain suitable pharmaceutically acceptable excipients as described supra.

Another formulation for use in the methods of the present disclosure employs transdermal delivery devices ("patches"). Such transdermal patches may be used to provide continuous or discontinuous infusion of the compounds of the present disclosure in controlled amounts. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

Compositions of the current disclosure can be formulated as pharmaceutical compositions which are suitable for intravenous administration. For intravenous administration, the compositions can be formulated in aqueous media using water-immiscible solvents, solubilizers, emulsifiers, surfactants or other solubilizing agents. Individual formulations may include one or more additional components such as stabilizers, tonicity modifiers, bases or acids to adjust pH, and solubilizers. The formulations can also optionally contain a preservative, such as ethylenediaminetetraacetic acid (EDTA) or sodium metabisulfate, to prevent the growth of microorganisms.

Pharmaceutical formulations may include stabilizing agents, which can be considered as co-emulsifiers. Anionic stabilizers include phosphatidylethanolamines, conjugated with polyethylene glycol, (PEG-PE) and phosphatidylglycerols, a specific example of which is dimyristolphosphatidylgylcerol (DMPG). Additional examples of useful stabilizers include oleic acid and its sodium salt, cholic acid and deoxycholic acid and their respective salts, cationic lipids such as stearylamine and oleylamine, and 3β-[N-(N',N'-dimethylaminoethane)carbamoyl]cholesterol (DC-Chol).

A pharmaceutical composition of the disclosure can be made isotonic with blood by the incorporation of a suitable tonicity modifier. A pharmaceutical composition of the disclosure may have a pH of about 1, 2, 3, 4, 5, 6, 7, 8, 9, 10, 11, 12, 13, or 14, as measured by, for example, a pH probe or pH paper. A composition may have a pH from about 4 to about 10. A pharmaceutical composition may be formulated to be at physiologically neutral pH.

Solutions containing the compounds of the present disclosure may be administered by injection or infusion, using suitable devices such as regular syringes or infusion devices, in the form of a pharmaceutical preparation which contains at least one compound of the disclosure either as a free base or as a pharmaceutically acceptable, non-toxic acid addition salt, such as for example hydrochloride, lactate, acetate, sulfamate, in combination with a pharmaceutically acceptable carrier.

Compositions of the current disclosure may be formulated into solutions for injection or infusion or infiltration. These solutions may contain stabilizing agents, antibacterial agents, buffering agents and may be manufactured in different dosage unit ampoules, single-use syringes or bottles.

The compounds of the present disclosure, or their pharmaceutically acceptable salts, are administered in a therapeutically-effective amount. It will be understood, however, that the amount of the compound actually administered will be determined by a physician or clinician, in the light of the relevant circumstances, including the condition to be treated, the chosen route of administration, the compound administered and its relative activity, the age, weight, and response of the individual patient, the severity of the patient's symptoms, and the like.

In some embodiments, a method of making a pharmaceutical composition, comprises combining a weight % of salicylic acid, or a salt thereof, from about 25% to about 30%, wherein the weight % of salicylic acid is based on a weight % of the composition, a molecule comprising an oxo group and an acidic group, or ester or salt thereof, and a halogen containing moiety.

A compound of the present disclosure can be prepared by a method well-known to those skilled in the art. However, methods for preparing the composition of the present disclosure are not limited to those described in the examples, and appropriate alterations and modifications can be added to these methods.

Indications

Compositions of the current disclosure may be used to treat an infection.

In some embodiments, a composition of the current disclosure is may be used to treat a skin infection. The skin infection may be caused by a bacterium, a virus, or a fungus. Bacterial skin infections include, but are not limited to, leprosy, carbuncles, *Staphylococcus aureus* infection, cellulitis, impetigo, boils, pilonidal cyst, abscess, or combinations thereof. Fungal skin infections include, but are not limited to, ringworm, athlete's foot, yeast infection, sporotrichosis, fungal nail infection, or combinations thereof.

In some embodiments, a composition of the current disclosure is used to treat a skin condition, wherein the skin conditions is rosacea. The skin infection may be caused by exposure to extreme temperatures, exercise, heat from sunlight, sunburns, stress, anxiety, cold wind, or combinations thereof.

Viral skin infections include, but are not limited to, molluscum contagiosum, shingles, chickenpox, herpes simplex virus, human papillomavirus, herpes zoster, molluscum contagiosum virus, human herpesvirus-3, and varicella. In some embodiments, the skin infection is caused by a virus. In some embodiments, the virus is selected from the group consisting of herpes simplex virus, human papillomavirus, herpes zoster, molluscum contagiosum virus, human herpesvirus-3, and varicella. In some embodiments, the skin infection is caused by the molluscum contagiosum virus. In some embodiments, the skin infection is caused by the human papillomavirus. In some embodiments, the skin infection is a wart, verruca vulgaris, verrucae, Plantar's warts, or squamous cell papilloma. In some embodiments, a composition of the current disclosure is used to treat a skin infection, wherein the skin infection is a wart. In some embodiments, the skin infection is benign or non-cancerous. Skin infections of the current disclosure may be contagious.

In some embodiments, the skin infection is cancerous. Skin infections of the current disclosure may be noncontagious. In some embodiments, the skin infection is cancer. In some embodiments, a composition of the current disclosure is used to treat cancer. In some embodiments, the skin infection may be cancer of the cervix, cancer of the vulva, cancer of the vagina, cancer of the penis, cancer of the oropharynx or cancer of the anus. In some embodiments, the current disclosure provides a method of preventing a cancer initiated by a virus, comprising application a composition of the current disclosure to a cell infected with a virus.

In some embodiments, the composition of the current disclosure retains greater than 50% of a keratolytic agent after placement in a sealed container for 6 months at a temperature of about 25° C. and a relative humidity level of about 50%. In some embodiments, the composition of the current disclosure retains at least 80% of the keratolytic agent after placement in a sealed container for 6 months at a temperature of about 25° C. and a relative humidity level of about 50%.

A composition of the current disclosure may be packaged into a container selected from the group consisting of a tube, a jar, a vial, a bag, a tray, a drum, a bottle, a syringe, and a can. In some embodiments, a composition of the current disclosure may be packaged into a tube. In some embodiments, a composition of the current disclosure may be packaged into a tube, wherein the tube contains information describing directions for use. In some embodiments, a composition of the current disclosure may be packaged into a tube, wherein the tube contains information describing directions for use, wherein the directions for use are for treating a wart.

Kits with unit doses of one or more of the compounds described herein are provided. Such kits may include a container containing a unit dose, an informational package insert describing the use and attendant benefits of the drugs in treating the disease, and optionally an appliance or device for delivery of the composition.

The kit may further comprise any device suitable for administration of the composition. For example, a kit comprising a topical formulation of pharmaceutical compositions may comprise gel suitable for topical administration and an alcohol wipe for sterilization of the application site.

In some cases, kits may be provided with instructions. The instructions may be provided in the kit or they may be accessed electronically (e.g., on the World Wide Web). The instructions may provide information on how to use the compositions of the present disclosure. In some embodiments, the kit comprises instructions for use in treating a wart. The instructions may provide information on how to perform the methods of the disclosure. In some embodiments, the kit comprises instructions for methods of treating a wart. In some cases, the instructions may provide dosing information. The instructions may provide drug information such as the mechanism of action, the formulation of the drug, adverse risks, contraindications, and the like. In some cases, the kit may be purchased by a physician or health care provider for administration at a clinic or hospital.

Figure 3:
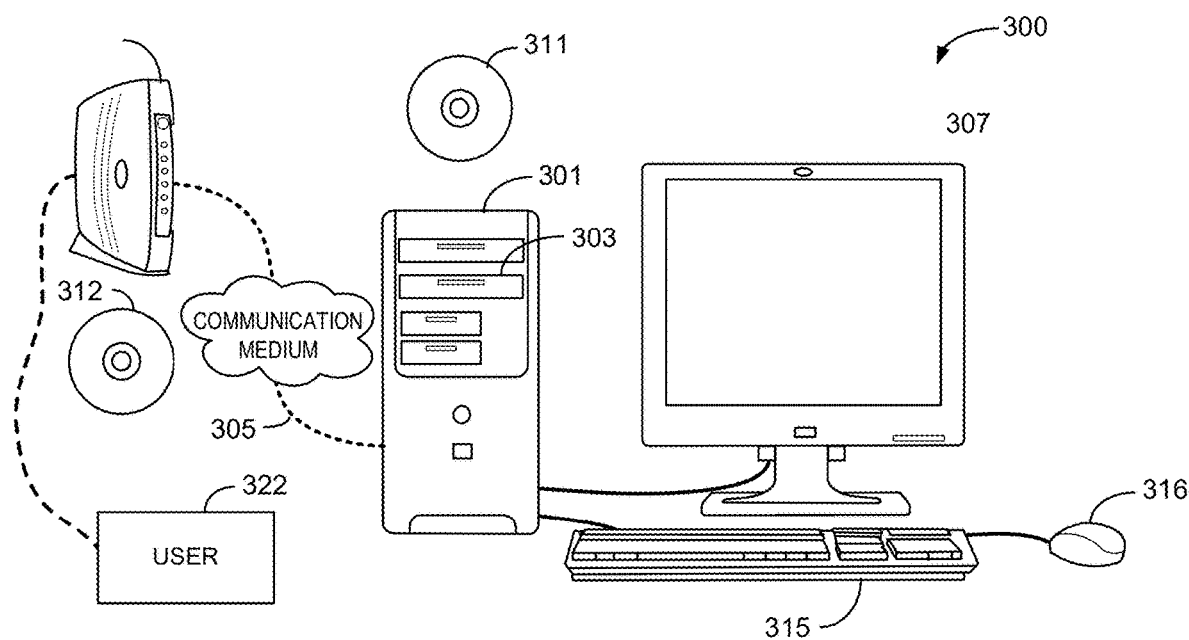
FIG. 3 illustrates an example of a computer system that can be used in connection with embodiments of the present disclosure.

The computer system 300 illustrated in FIG. 3 may be understood as a logical apparatus that can read instructions from media 311 and/or a network port 305, which can optionally be connected to server 309 having fixed media 312. The system, such as shown in FIG. 3 can include a CPU 301, disk drives 303, optional input devices such as keyboard 315 and/or mouse 316 and optional monitor 307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 322 as illustrated in FIG. 3.

EXAMPLES

The following examples are given for the purpose of illustrating various embodiments of the disclosure and are not meant to limit the present disclosure in any fashion. The present examples; along with the methods described herein are presently representative of preferred embodiments; are exemplary; and are not intended as limitations on the scope of the disclosure. Changes therein and other uses which are encompassed within the spirit of the disclosure as defined by the scope of the claims will occur to those skilled in the art.

Example 1: Preparation of from about 0.4 Parts to about 0.6 Parts Povidone Iodine USP, 12.0 Parts to About 18.0 Parts Ethyl Pyruvate, and 13.6 Parts to About 20.4 Parts Salicylic Acid in 100 Parts of the Pharmaceutically Effective Composition For Treatment of Infection The pharmaceutically effective composition includes from about 0.4 parts to about 0.6 parts povidone iodine USP, 12.0 parts to about 18.0 parts ethyl pyruvate, and 13.6 parts to about 20.4 parts salicylic acid USP in 100 parts of the pharmaceutically effective composition for treatment of infection. The components/compositions are provided in Table 1 that follows.

TABLE 1

Unit/Batch Composition

| Ingredient | Amount/ 100 ml | Per Batch | [a] | Percent |
| --- | --- | --- | --- | --- |
| Isopropyl Alcohol [b] | 26.6-40.8 ml | 0.266-0.408 ml | | 26.6-40.8% |
| 2-(2-Ethoxyethoxy) ethanol NF (Transcutol P) [c] | 20.0-30.0 ml | 0.20-0.3 ml | | 20-30% |
| Ethyl pyruvate [d] | 12.0-18.0 ml | 0.12-0.18 ml | | 12.0-18.0% |
| Propylene Glycol (1,2 dihydroxy Propane) [e] | 4.2-5.8 gm | 0.042-0.058 g | | 4.2-5.8% |
| Glycerin USP [f] | 0.8-1.2 ml | 0.008-0.012 ml | | 0.8-1.2% |
| Salicylic Acid USP [g] | 13.6-20.4 gm | 0.136-0.20 g | | 13.6-20.4% |
| Butylated Hydroxytoluene NF (BHT) [h] | 0.32-0.48 gm | 0.032-0.048 g | | 3.2-4.8% |
| Hydroxypropylcellulose NF 1500 CPS | 1.44-2.16 gm | 0.0144-0.0216 g | | 1.44-2.16% |
| Povidone Iodine USP | 0.4-0.6 gm | 0.004-0.006 g | | 0.4-0.6% |
| Triethanolamine | 0.24-0.36 gm | 0.0024-0.0036 g | | 0.24-0.36% |

[a] Slight overages of the drug substances may be used as required to offset losses during manufacture.
[b] Available from Nexeo Solutions, Rensselaer, NY 12144.
[c] Available from Gattefosse, Paramus, NJ 07652.
[d] Available from Spectrum Fine Chemcals, New Brunswick, NJ 08901-3605.
[e] Available from Kraft Chemical, Melrose Park, IL 60160.
[f] Available from Jeen Chemical, Fairfield, NJ 07004.
[g-i] Available from Spectrum Fine Chemcals, New Brunswick, NJ 08901-3605.
[j] Available from Astro Chemcals, Springfield, MA 01104.

A pharmaceutically effective composition, in 100 parts, having from about 0.4 parts to about 0.6 parts povidone iodine USP, 12.0 parts to about 18.0 parts ethyl pyruvate, and 13.6 parts to about 20.4 parts salicylic acid USP may be formulated by mixing the components listed in Table 1, supra, according to the following general method 200.

In step 1 of the method 200, isopropyl alcohol, 2-(2-ethoxyethoxy) ethanol NF (Transcutol P), ethyl pyruvate, propylene glycol (1,2 dihydroxy Propane), Glycerin USP, salicylic acid USP, and butylated hydroxy toluene (BHT NF) are incrementally added with mixing in a high shear mixer for 30 minutes, forming a solution. In step 2 of the method 200, hydroxypropyl cellulose NF(HPC) is incrementally added to the solution of step 1 with continued mixing, resulting in a thickened mixture. In step 3 of the method 200, povidone Iodine USP and triethanolamine are incrementally added to the thickened mixture of step 2 with mixing, forming a thickened mixture that may be topically applied to an infection of the skin, e.g., a wart.

The pharmaceutically effective composition having, in 100 parts, from about 0.4 parts to about 0.6 parts povidone iodine USP, 12.0 parts to about 18.0 parts ethyl pyruvate, and 13.6 parts to about 20.4 parts salicylic acid USP and formulated by mixing the components listed in Table 1, supra, according to the general method 200, was topically applied to a total of 12 patients (n=12) having documented warts. These resistant wart patients had been previously treated with at least one therapy. Treatment in accordance with the method 100 resulted in a higher cure rate than would be achieved if the infection were treated by topically applying a control composition having only the keratolytic and balance being the pharmaceutically acceptable excipient.[1] Patients ranged in age from 14 to 66 years old. The pharmaceutically effective composition of the present disclosure was exclusively used by patients to treat their verrucae of the lower extremity, including: the knee, lower leg, ankle, foot, and toes. No other treatments were provided. Biopsies were performed on most patients and confirmed verruca in all patients that were biopsied.

During the course of the study period, patients were instructed to use the pharmaceutically effective composition of the present disclosure, in the morning after a shower with a Band-Aid and at night before bed without occlusion. The patient was further instructed to self-debride daily with a file or pumice stone before application, wash and dry the area well before application, and change socks and shoes twice daily. The patient was seen every 2 weeks for reevaluation, debridement, and application in the office.

Following completion of the study and resolution of the warts, the patient was seen 2 weeks post-clearing for reevaluation, 4 weeks post-clearing for an additional check and at 8 weeks post-clearing for a final reevaluation confirming complete resolution before discharge.

Of the 12 patients treated with the pharmaceutically effective composition of the present disclosure, in our practice, all warts resolved, with most in 2-6 weeks. Of particular note was a very difficult case that involved 2 large mosaic verruca measuring 2 cm×3 cm on the plantar medial hallux and 4 cm×5 cm plantar heel respectively that were resistant to multiple therapies for 14 months. Previous treatments by 2 podiatrists and a dermatologist were unsuccessful using oral Vitamin A, oral cimetidine, a variety of topicals, laser and Candin injections. Biopsy confirmed diagnosis of verruca. After 20 weeks of being treated with the pharmaceutically effective composition of the present disclosure all lesions resolved with no reoccurrence.

We note of particular importance when using the pharmaceutically effective composition of the present disclosure was ensuring a lag time between showering and application and a lag time between application and putting on socks and shoe-gear. In addition we note that it is important to emphasize to patients to rub the pharmaceutically effective composition of the present disclosure well into and on the treated lesion and letting it dry before proceeding with daily activities.

Alternatively, a pharmaceutically effective composition, in 100 parts, for treating skin infections may be prepared according to the method 200, advantageously having in 100 parts of the composition, 0-99 parts of a pharmaceutically acceptable excipient, 49.9-10 parts of a keratolytic, 50-5 parts ethyl pyruvate, and 19-0.1 parts povidone iodine. The components/compositions are provided in Table 2, as follows.

TABLE 2

Unit/Batch Composition

| Ingredient | Amount/ 100 ml | Per Batch [a] | Percent |
|---|---|---|---|
| Isopropyl Alcohol [b] | 20.0-30.0 ml | 0.2-0.3 ml | 20.0-30.0% |
| 2-(2-Ethoxyethoxy) ethanol NF (Transcutol P) [c] | 20.0-30.0 ml | 0.20-0.3 ml | 20-30% |
| Ethyl pyruvate [d] | 12.0-18.0 ml | 0.12 -0.18 ml | 12.0-18.0% |
| Propylene Glycol (1,2 dihydroxy Propane) [e] | 1.6-2.4 gm | 0.016-0.024 g | 1.6-2.4% |
| Glycerin USP [f] | 0.8-1.2 ml | 0.008-0.012 ml | 0.8-1.2% |
| Salicylic Acid USP [g] | 23.2-28.8 gm | 0.232-0.288 g | 23.2-28.8% |
| Butylated Hydroxytoluene NF (BHT) [h] | 0.32-0.48 gm | 0.032-0.048 g | 3.2-4.8% |
| Hydroxypropylcellulose NF 1500 CPS | 1.44-2.16 gm | 0.0144-0.0216 g | 1.44-2.16% |
| Povidone Iodine USP | 0.4-0.6 gm | 0.004-0.006 g | 0.4-0.6% |
| Triethanolamine | 0.24-0.36 gm | 0.0024-0.0036 g | 0.24-0.36% |

[a] Slight overages of the drug substances may be used as required to offset losses during manufacture.
[b] Available from Nexeo Solutions, Rensselaer, NY 12144.
[c] Available from Gattefosse, Paramus, NJ 07652.
[d] Available from Spectrum Fine Chemcals, New Brunswick, NJ 08901-3605.
[e] Available from Kraft Chemical, Melrose Park, IL 60160.
[f] Available from Jeen Chemical, Fairfield, NJ 07004.
[g-i] Available from Spectrum Fine Chemcals, New Brunswick, NJ 08901-3605.
[j] Available from Astro Chemcals, Springfield, MA 01104.

FIG. 2 depicts results from topical treatment of resistant wart patients in accord with the method 100. The chart of FIG. 2 illustrates percent cure of warts (verrucae) in accordance with the method 100. Approximately 80% of resistant warts cleared in just 2-6 week. Approximately 90.9% of the warts in the patients cleared; n=11, in 4-6 weeks.

The foregoing description of the embodiments of this disclosure has been presented for purposes of illustration and description. It is not intended to be exhaustive or to limit the disclosure to the precise form disclosed, and obviously, many modifications and variations are possible. Such modifications and variations that may be apparent to a person skilled in the art are intended to be included within the scope of this disclosure as defined by the accompanying claims.

Example 3: Liquid Formulation

A composition of the current disclosure may be formulated as a liquid for topical administration with the composition listed in Table 3.

TABLE 3

Liquid formulation

| Ingredient | Quantity |
|---|---|
| Sodium chloride | 0.9 g/100 mL |
| Salicylic acid | 13 g/100 mL |
| Ethyl pyruvate | 12 mL/100 mL |
| Polyvinylpyrrolidone-iodine | 0.4 g/100 mL |
| Methylparaben | 1 mg/mL |
| Compound of Formula I | 0.5 g/100 mL |
| Water | Up to 100 mL |

Example 4: Paste Formulation

A composition of the current disclosure may be formulated as a paste for topical administration with the composition listed in Table 4.

TABLE 4

| Paste formulation | |
|---|---|
| Ingredient | Quantity (mol %) |
| Zinc oxide | 25 |
| Starch | 25 |
| Salicylic acid | 20 |
| Ethyl pyruvate | 12 |
| Polyvinylpyrrolidone-iodine | 0.2 |
| Calamine | 5 |
| White petroleum | 12.8 |

Example 5: Paste Formulation

A composition of the current disclosure may be formulated as a paste for topical administration with the composition listed in Table 5.

TABLE 5

| Paste formulation | |
|---|---|
| Ingredient | Quantity |
| Zinc oxide | 20 g |
| Starch | 20 g |
| Salicylic acid | 13.6 g |
| Ethyl pyruvate | 12 mL |
| Polyvinylpyrrolidone-iodine | 0.4 g |
| Calamine | 3 g |
| White petroleum | 10 g |

Example 6: Ointment Formulation

A composition of the current disclosure may be formulated as an ointment for topical administration with the composition listed in Table 6.

TABLE 6

| Ointment formulation | |
|---|---|
| Ingredient | Quantity (mol %) |
| Salicylic acid | 28 |
| Ethyl pyruvate | 12 |
| Polyvinylpyrrolidone-iodine | 0.6 |
| White wax | 5 |
| White petroleum | 54.4 |

Example 7: Ointment Formulation

A composition of the current disclosure may be formulated as an ointment for topical administration with the composition listed in Table 7.

TABLE 7

| Ointment formulation | |
|---|---|
| Ingredient | Quantity (weight %) |
| Salicylic acid | 28.8 |
| Ethyl pyruvate | 20 |
| Polyvinylpyrrolidone-iodine | 0.6 |
| White wax | 5 |
| White petroleum | 45.6 |

Example 8: Cream Formulation

A composition of the current disclosure may be formulated as a cream for topical administration with the composition listed in Table 8.

TABLE 8

| Cream formulation | |
|---|---|
| Ingredient | Quantity (weight %) |
| Almond oil | 35 |
| White wax | 20 |
| Salicylic acid | 28 |
| Ethyl pyruvate | 12 |
| Polyvinylpyrrolidone-iodine | 0.2 |
| Rose water | 2 |
| Rose oil | 0.02 |
| Water | 2.78 |

Example 9: Gel Formulation

A composition of the current disclosure may be formulated as a gel for topical administration with the composition listed in Table 9.

TABLE 9

| Gel formulation | |
|---|---|
| Ingredient | Quantity (mol %) |
| Salicylic acid | 28 |
| Propylene glycol | 20 |
| Ethyl pyruvate | 12 |
| Polyvinylpyrrolidone-iodine | 0.2 |
| Methylparaben | 0.015 |
| Purified water | 39.785 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method for treating a viral wart in a subject in need thereof, comprising administering to the subject a therapeutically effective amount of a pharmaceutical composition, wherein the pharmaceutical composition comprises:
   a) about 15 weight % to about 30 weight % of a keratolytic agent comprising salicylic acid, an ester thereof, or a salt thereof, wherein the weight % of the keratolytic agent is based on a total weight % of the composition;
   b) about 10 weight % to about 20 weight % of a molecule comprising a pyruvate group that is methyl pyruvate, ethyl pyruvate, or propyl pyruvate, wherein the weight % of the molecule comprising the pyruvate group is based on a total weight % of the composition;
   c) about 0.1 weight % to about 1 weight % of polyvinylpyrrolidone-iodine, wherein the weight % of the polyvinylpyrrolidone-iodine is based on a total weight % of the composition; and
   d) at least 35 weight % of an organic solvent comprising one or more alcohols.

2. The method of claim 1, wherein the keratolytic agent further comprises pyruvic acid, chloroacetic acid, trichloroacetic acid, menthol, acetic acid, ascorbic acid, pantothenic acid, lactic acid, or a salt of any of the above.

3. The method of claim 1, wherein the pharmaceutical composition comprises about 17 weight % of the keratolytic agent.

4. The method of claim 1, wherein the molecule comprising the pyruvate group is the ethyl pyruvate.

5. The method of claim 1, wherein the pharmaceutical composition comprises about 15 weight % of the molecule comprising the pyruvate group.

6. The method of claim 1, wherein the pharmaceutical composition comprises about 0.5 weight % of the polyvinylpyrrolidone-iodine.

7. The method of claim 1, wherein the pharmaceutical composition comprises at least about 40 weight % of the organic solvent.

8. The method of claim 1, wherein the pharmaceutical composition further comprises a pharmaceutically acceptable excipient.

9. The method of claim 8, wherein the pharmaceutically acceptable excipient comprises glycerin, propylene glycol, transcutol, triethanolamine, or hydroxypropyl cellulose.

10. The method of claim 1, wherein the pharmaceutical composition further comprises transcutol.

11. The method of claim 1, wherein the pharmaceutical composition further comprises nitrocellulose.

12. The method of claim 1, wherein the pharmaceutical composition further comprises polyethylene glycol.

13. The method of claim 1, wherein the pharmaceutical composition further comprises butylated hydroxy toluene.

14. The method of claim 1, wherein the pharmaceutical composition is formulated for topical administration.

15. The method of claim 1, wherein the subject is a human.

* * * * *